US008871800B2

(12) United States Patent (10) Patent No.: US 8,871,800 B2
Rongen et al. (45) Date of Patent: Oct. 28, 2014

(54) STATIN AND OMEGA-3 FATTY ACIDS FOR REDUCTION OF APO-B LEVELS

(75) Inventors: Roelof M. L. Rongen, Califon, NJ (US); Robert A. Shalwitz, Bexley, OH (US); Douglas Kling, Parsippany, NJ (US); Ralph T. Doyle, Jr., Milford, NJ (US)

(73) Assignee: GlaxoSmithKline, LLC, Wilmington, DE (US)

( * ) Notice: Subject to any disclaimer, the term of this patent is extended or adjusted under 35 U.S.C. 154(b) by 719 days.

(21) Appl. No.: 12/561,558

(22) Filed: Sep. 17, 2009

(65) Prior Publication Data

US 2010/0010026 A1 Jan. 14, 2010

Related U.S. Application Data

(63) Continuation of application No. 11/851,867, filed on Sep. 7, 2007, now abandoned, which is a continuation-in-part of application No. 11/742,292, filed on Apr. 30, 2007, now abandoned.

(60) Provisional application No. 60/850,280, filed on Oct. 10, 2006.

(51) Int. Cl.

| A61K 31/202 | (2006.01) |
| A61K 31/351 | (2006.01) |
| A61K 31/366 | (2006.01) |
| A61K 31/405 | (2006.01) |
| A61K 31/20 | (2006.01) |
| A61K 31/35 | (2006.01) |
| A61K 31/47 | (2006.01) |
| A61K 31/225 | (2006.01) |
| A61K 31/401 | (2006.01) |
| A61K 31/232 | (2006.01) |
| A61K 31/40 | (2006.01) |
| A61K 31/22 | (2006.01) |
| A61K 31/505 | (2006.01) |

(52) U.S. Cl.
CPC ............. *A61K 31/20* (2013.01); *A61K 31/366* (2013.01); *A61K 31/202* (2013.01); *A61K 31/405* (2013.01); *A61K 31/351* (2013.01); *A61K 31/35* (2013.01); *A61K 31/47* (2013.01); *A61K 31/225* (2013.01); *A61K 31/401* (2013.01); *A61K 31/232* (2013.01); *A61K 31/40* (2013.01); *A61K 31/22* (2013.01); *A61K 31/505* (2013.01)
USPC .......................................... 514/460; 514/558

(58) Field of Classification Search
CPC .................... A61K 31/351; A61K 31/202
See application file for complete search history.

(56) References Cited

U.S. PATENT DOCUMENTS

| 7,022,713 B2 | 4/2006 | Aoki et al. |
| 2002/0016312 A1 | 2/2002 | Seed et al. |
| 2003/0170643 A1 | 9/2003 | Fischer et al. |
| 2004/0018248 A1 | 1/2004 | Bendich |
| 2006/0034815 A1 | 2/2006 | Guzman et al. |
| 2006/0211762 A1 | 9/2006 | Rongen et al. |
| 2006/0211763 A1 | 9/2006 | Fawzy et al. |
| 2007/0021504 A1 | 1/2007 | Yokoyama et al. |

FOREIGN PATENT DOCUMENTS

WO   WO 2006/013602 A1   2/2006

OTHER PUBLICATIONS

"Third Report of the National Cholesterol Education Program Expert Panel on Detection, Evaluation, and Treatment of High Blood Cholesterol in Adults," NIH Publication No. 02-5215 (2002) ("NCEP ATP III").
Nakamura et al., "Joint effects of HMG-CoA reductase inhibitors and eicosapentaenoic acids on serum lipid profile and plasma fatty acid concentrations in patients with hyperlipidemia," *Int. J. Clin. Lab Res.* 29:22-25 (1999).
Davidson et al., "Separate and Joint Effects of Marine Oil and Simvastatin in Patients with Combined Hyperlipidemia," *Am. J. Cardiol.* 80: 797-798 (1997).
Hong et al., "Effects of Simvastatin Combined with Omega-3 Fatty Acids on High Sensitive C-Reactive Protein, Lipidemia, and Fibrinolysis in Patients with Mixed Dyslipidemia," *Chin. Med. Sci. J.* 19:145-49 (2004).
Contacos et al., "Effect of Pravastatin and $\psi$-3 Fatty Acids on Plasma Lipids and Lipoproteins in Patients with Combined Hyperlipidemia," *Arterioscl. Thromb.* 13:1755-62 (1993).
Singer, "Letter to the Editor: Fluvastatin plus fish oil more effective on cardiovasular risk factors than fluvastatin alone," *Prost Leukotr. Ess. Fatty Acids* 72:379-80 (2005).
Liu et al., "Effects of stable fish oil and simvastatin on plasma lipoproteins in patients with hyperlipidemia," *Nutrition Research* 23:1027-1034 (2003).
Grekas et al., "Combined Treatment with Low-Dose Pravastatin and Fish Oil in Post-Renal Transplantation Dyslipidemia," *Nephron* 88:329-333 (2001).
Howe et al., "Effects of Fish Oil Supplementation in Statin-Treated Subjects with Persistent Hypertriglyceridaemia," *Clin. Exp. Pharmacol. Physiol.*, 29:A50-A51 (2002) (Abstract only).

(Continued)

Primary Examiner — James D Anderson
(74) *Attorney, Agent, or Firm* — Loretta J. Sauermelch; Alan X. Scrivner

(57) ABSTRACT

Methods of utilizing a combined administration or a unit dosage of a combination of an HMG-CoA inhibitor and omega-3 fatty acids for the reduction of apolipoprotein-B levels. The methods are especially useful in the treatment of patients with hypertriglyceridemia or hypercholesterolemia or mixed dyslipidemia, coronary heart disease (CHD), vascular disease, atherosclerotic disease and related conditions, and for the prevention or reduction of cardiovascular, cardiac, and vascular events.

30 Claims, No Drawings

(56) References Cited

OTHER PUBLICATIONS

Sandset et al., "Treatment with Hydroxymethylglutaryl-Coenzyme A Reductase Inhibitors in Hypercholesterolemia Induces Changes in the Components of the Extrinsic Coagulation System," *Arterioscler. Thromb. Vasc. Biol.* 11:138-45 (1991).
Tomei et al., "Efficacy and Tolerability of Simvastatin and Omega-3 Fatty Acids in Patients with Coronary Disease, Hypercholesterolemia and Hypertriglyceridemia," *Cardiologia*, 38: 773-78 (1993) (Abstract only).
Nordoy et al., "Effects on Serum Lipids and Bleeding Time of n-3 Fatty Acids and Cholesterol-Lowering Drugs in Patients with Familial Hypercholesterolemia (Type IIa) Exposed to Physical Exercise," *Hypercholesterolemia, Exercise and n-3 Fatty Acids*, 252-56 (1992).
Hansen et al., "Tissue-Factor Pathway Inhibitor and Lipoproteins: Evidence for Association with and Regulation by LDL in Human Plasma," *Arteriosclerosis and Thrombosis* 14(2): 223-229 (1994).
Nordoy et al., "Effects of atorvastatin and ψ-3 fatty acids on LDL subtractions and postprandial hyperlipemia in patients with combined hyperlipemia," *Nutr. Metab. Cardiovasc. Dis.* 11:7-16 (2001).
Salvi et al., "Effects of Fish Oil on Serum Lipids and Lipoprotein(A) Levels in Heterozygous Familial Hypercholesterolemia," *Curr. Ther. Res.* 53:717-21 (1993).
Bhatnagar et al., "Treatment of mixed hyperlipidaemia using a combination of omega-3 fatty acids and HMG CoA reductase inhibitor," *Eur. Heart J Supplements* 4(Suppl. D):D53-D58 (2001).
Chan et al., "Regulatory Effects of HMG CoA Reductase Inhibitor and Fish Oils on Apolipoprotein B-100 Kinetics in Insulin-Resistant Obese Male Subjects with Dyslipidemia," *Diabetes*, 51:2377-2386 (2002).
Chan et al., "Factorial Study of the effects of atorvastatin and fish oil on dyslipidaemia in visceral obesity," *Eur. J of Clin. Invest.* 32:429-436 (2002).
Nordoy et al., "n-3 Fatty Acids as Supplement to Statins in the Treatment of Patients with Combined Hyperlipidemia," *Essent. Fatty Acids Eicosanoids, Invited Pap. Int'l Congr. 4th*, 256-61 (1998).
Nordoy et al., "Effects of Simvastatin and omega-3 fatty acids on plasma lipoproteins and lipid peroxidation in patients with combined hyperlipidaemia," *J. of Internal Medicine*, 243:163-170 (1998).
Durrington et al., "An omega-3 polyunsaturated fatty acid concentrate administered for one year decreased triglycerides in simvastatin treated patients with coronary heart disease and persisting hypertriglyceridaemia," *Heart*, 85:544-548 (2001).
Huff et al., "Dietary fish oil plus lovastatin decreases both VLDL and LDL apo B production in miniature pigs;" *Arterioscler. Thromb.*, 12(8):902-10 (1992).
Yano et al., "Effects of ethyl-all-cis-5,8,11,14,17-icosapentaenoate (EPA-E), pravastatin and their combination on serum lipids and intimal thickening of cuff-sheathed carotid artery in rabbits," *Life Sci.*, 61(20):2007-15 (1997) (Abstract only).
Das, "Essential fatty acids as possible mediators of the actions of statins," *Prostaglandins Leukot. Essent. Fatty Acids*, 65(1):37-40 (2001) (Abstract only).
Nordoy, "Statins and omega-3 fatty acids in the treatment of dyslipidemia and coronary heart disease," *Minerva Med.*, 93(5):357-63 (2002) (Abstract only).
Nordoy et al., "Atorvastatin and omega-3 fatty acids protect against activation of the coagulation system in patients with combined hyperlipemia," *J. Thromb. Haemost.*, 1(4):690-7 (2003) (Abstract only).
Yokoyama et al., "Effects of eicosapentaenoic acid on cardiovascular events in Japanese patients with hypercholesterolemia: rationale, design, and baseline characteristics of the Japan EPA Lipid Intervention Study (JELIS)," *Am. Heart J.*, 146(4):613-620 (2003) (Abstract only).
McKenney et al., "Study of the pharmacokinetic interaction between simvastatin and prescription omega-3-acid ethyl esters," *J. Clin. Pharmacol*, 46(7):785-91 (Jul. 2006) (Abstract only).
Nambi et al., "Combination therapy with statins and omega-3 fatty acids," *Am. J. Cardiol*, 98(4A):34i-38i (Aug. 2006) (Abstract only).
Bays, "Clinical overview of Omacor: a concentrated formulation of omega-3 polyunsaturated fatty acids," *Am. J. Cardiol*, 98(4A):71i-76i (Aug. 2006) (Abstract only).
Sniderman, "How, when, and why to use apolipoprotein B in clinical practice," *Am. J. Cardiol.* 90(suppl):48i-54i (2002).
Jula et al., "Effects of Diet and Simvastatin on Serum Lipids, Insulin, and Antioxidants in Hypercholesterolemic Men," *JAMA* 287(5): 598-605 (2002).
Drug Approval Package: Omacor (Omega-3-Acid Ethyl Esters) NDA #021654; online U.S. Food & Drug Administration, Drugs@FDA (LOVAZA); Date created Jan. 5, 2005—Cover sheet and Medical Review(s) section.
Drug Approval Package: Omacor NDA #021853 & 021654s016; online U.S. Food & Drug Administration, Drugs@FDA (LOVAZA); Date created Nov. 19, 2009—Cover sheet and Medical Review(s) section.

STATIN AND OMEGA-3 FATTY ACIDS FOR REDUCTION OF APO-B LEVELS

The present application is a continuation of U.S. application Ser. No. 11/851,867, filed Sep. 7, 2007, now abandoned which is a continuation-in-part of U.S. application Ser. No. 11/742,292, filed Apr. 30, 2007, now abandoned and claims priority to provisional patent application Ser. No. 60/850,280, filed Oct. 10, 2006, the disclosures of which are hereby incorporated by reference.

FIELD OF THE INVENTION

The present invention relates to a method utilizing a combined administration or a unit dosage of a combination of an HMG-CoA inhibitor and omega-3 fatty acids for the reduction of apolipoprotein-B (Apo-B) levels. This method is especially useful in the treatment of patients with hypertriglyceridemia or hypercholesterolemia or mixed dyslipidemia, coronary heart disease (CHD), vascular disease, atherosclerotic disease and related conditions, and for the prevention or reduction of cardiovascular, cardiac, and vascular events.

BACKGROUND OF THE INVENTION

In humans, cholesterol and triglycerides are part of lipoprotein complexes in the bloodstream, and can be separated via ultracentrifugation into high-density lipoprotein (HDL), intermediate-density lipoprotein (IDL), low-density lipoprotein (LDL) and very-low-density lipoprotein (VLDL) fractions. Cholesterol and triglycerides are synthesized in the liver, incorporated into VLDL, and released into the plasma. High levels of total cholesterol (total-C), LDL-C, and apolipoprotein-B (Apo-B, a membrane complex for LDL-C and VLDL-C) promote human atherosclerosis and decreased levels of HDL-C and its transport complex, apolipoprotein-A (Apo-A), which are associated with the development of atherosclerosis. Further, cardiovascular morbidity and mortality in humans can vary directly with the level of TC and LDL-C and inversely with the level of HDL-C. In addition, researchers have found that non-HDL cholesterol (non-HDL-C), which is determined by the subtraction of HDL-C from TC, is an important indicator of hypertriglyceridemia, vascular disease, artherosclerotic disease and related conditions. Non-HDL-C particles contain Apo-B as the membrane-complexing apolipoprotein. Although non-HDL-C is a good measure for the total amount of cholesterol present in atherogenic Apo-B-containing particles, a direct measure of Apo-B may provide a better measure of the amount of atherogenic particles per unit of serum.

Although LDL-C remains the lipid value commonly used to assess cardiovascular risk, Apo-B may better reflect lipid risk. Sniderman, *Am. J. Cardiol.* 90(suppl):48i-54i (2002), reviews the evidence supporting the value of Apo-B in predicting coronary artery disease risk and its superiority over calculated LDL-C levels.

Cardiovascular disease (CVD) is a broad term that encompasses a variety of diseases and conditions. It refers to any disorder in any of the various parts of the cardiovascular system, which consists of the heart and all of the blood vessels found throughout the body. Diseases of the heart may include coronary artery disease, CHD, cardiomyopathy, valvular heart disease, pericardial disease, congenital heart disease (e.g., coarctation, atrial or ventricular septal defects), and heart failure. Diseases of the blood vessels may include arteriosclerosis, atherosclerosis, hypertension, stroke, vascular dementia, aneurysm, peripheral arterial disease, intermittent claudication, vasculitis, venous incompetence, venous thrombosis, varicose veins, and lymphedema. Some patients may have received treatment for their CVD, such as vascular or coronary revascularizations (angioplasty with or without stent placement, or vascular grafting). Some types of cardiovascular disease are congenital, but many are acquired later in life and are attributable to unhealthy habits, such as a sedentary lifestyle and smoking. Some types of CVD can also lead to further heart problems, such as angina, major adverse cardiovascular events (MACEs) and/or major coronary events (MCEs) such as myocardial infarction (MI) or coronary intervention, or even death (cardiac or cardiovascular), which underscores the importance of efforts to treat and prevent CVD.

Primary prevention efforts are focused on reducing known risk factors for CVD, or preventing their development, with the aim of delaying or preventing the onset of CVD, MACEs or MCEs. Secondary prevention efforts are focused on reducing recurrent CVD and decreasing mortality, MACEs or MCEs in patients with established CVD.

MACEs include cardiac death, other cardiovascular death, MCEs (which include myocardial infarction (MI) and coronary intervention such as coronary revascularization, angioplasty, percutaneous transluminal coronary angioplasty (PTCA), percutaneous coronary intervention (PCI) and coronary artery bypass graft (CABG)), hospitalization for unstable angina, stroke, transient ischemic attack (TIA) and hospitalization and/or intervention for peripheral artery disease (PAD).

The Third Report of the National Cholesterol Education Program Expert Panel on Detection, Evaluation, and Treatment of High Blood Cholesterol in Adults, NIH Publication No. 02-5215 (September 2002) (also known as the "NCEP ATP III"), hereby incorporated by reference, provides recommendations for cholesterol-lowering therapy in an effort to reduce risk of CHD. In the ATP III, CHD is defined as symptomatic ischemic heart disease, including MI, stable or unstable angina, demonstrated myocardial ischemia by non-invasive testing, and history of coronary artery procedures. The ATP III indicates that LDL-C is the primary target of lipid therapy, with other lipids to be controlled including triglycerides (TG), non-HDL-C and HDL-C. Apo-B is listed as an emerging risk factor. While the ATP III was not prepared to replace LDL-C as the primary target of lipid therapy, it noted that limited epidemiological and clinical trial evidence supports Apo-B's superiority over LDL-C in risk prediction.

A guiding principle of ATP III is that the intensity of LDL-C lowering therapy is adjusted to the individual's absolute risk for CHD. Risk assessment is broken down into short term (≤10-year) and long term (>10-year) risk of CHD, and the LDL-C goals are adjusted accordingly. In addition, ATP III identifies three categories of risk for CHD that modify LDL-C goals: established CHD and CHD risk equivalents, multiple (2+) risk factors, and 0-1 risk factor. Established CHD and CHD risk equivalents include CHD, other clinical atherosclerotic diseases, diabetes mellitus, and multiple risk factors and a 10-year risk for CHD >20 percent. The major independent risk factors identified in risk factor counting include cigarette smoking, hypertension, low HDL-C, family history of premature CHD and age.

The LDL-C goals for the three categories of risk factors are as follows:

| Risk Factors | LDL-C Goal |
| --- | --- |
| CHD and CHD Risk Equivalent | <100 mg/dl |
| Multiple (2+) Risk Factors | <130 mg/dl* |
| 0-1 Risk Factor | <160 mg/dl |

*LDL-C goal for multiple risk factor persons with 10-year risk >20 percent is <100 mg/dl.

The ATP III also outlines LDL-C goals for patients based on the percentage of 10-year risk for CHD:

| 10-Year Risk | LDL-C Goal |
| --- | --- |
| >20% | <100 mg/dl |
| 10-20% | <130 mg/dl |
| <10% and Multiple (2+) Risk Factors | <130 mg/dl |
| <10% and 0-1 Risk Factor | <160 mg/dl |

3-hydroxy-3-methyl glutaryl coenzyme A (HMG-CoA) reductase inhibitors (known as HMG-CoA inhibitors, or "statins"), have been used to treat hyperlipidemia and atherosclerosis, for example. Typically, statin monotherapy has been used to treat cholesterol levels, particularly when a patient is not at an acceptable LDL-C level. Statins inhibit the enzyme HMG-CoA reductase, which controls the rate of cholesterol production in the body. Statins lower cholesterol by slowing down the production of cholesterol and by increasing the liver's ability to remove the LDL-C already in the blood. Accordingly, the major effect of the statins is to lower LDL-C levels. Statins have been shown to decrease CHD risk by about one-third. However, statins only appear to have a modest effect on the TG-HDL axis.

Marine oils, also commonly referred to as fish oils, are a good source of two omega-3 fatty acids, eicosapentaenoic acid (EPA) and docosahexaenoic acid (DHA), which have been found to regulate lipid metabolism. Omega-3 fatty acids have been found to have beneficial effects on the risk factors for cardiovascular diseases, especially mild hypertension, hypertriglyceridemia and on the coagulation factor VII phospholipid complex activity. Omega-3 fatty acids lower serum triglycerides, increase serum HDL-cholesterol, lower systolic and diastolic blood pressure and the pulse rate, and lower the activity of the blood coagulation factor VII phospholipid complex. Further, omega-3 fatty acids seem to be well tolerated, without giving rise to any severe side effects.

One such form of omega-3 fatty acids is a concentrate of omega-3, long chain, polyunsaturated fatty acids from fish oil containing DHA and EPA and was sold under the trademark Omacor®, and is now known as Lovaza™. Such a form of omega-3 fatty acids is described, for example, in U.S. Pat. Nos. 5,502,077, 5,656,667 and 5,698,594, each incorporated herein by reference.

Patients with mixed dyslipidemia, hypertriglyceridemia and/or hypercholesteremia often present with blood levels of LDL-C greater than 190 mg/dl, triglyceride levels of 200 mg/dl or higher, and/or Apo-B levels of greater than 0.9 g/l. In many patients with hypertriglyceridemia, hypercholesterolemia and/or mixed dyslipidemia, the use of diet and single-drug therapy does not always decrease LDL-C, triglycerides and/or Apo-B levels adequately enough to reach targeted values. In these patients, a complementary combination therapy of a statin and omega-3 fatty acids may be desirable.

Many studies have examined the combined effects of omega-3 fatty acid and statin therapy on Apo-B levels. While most of these studies confirm that statins significantly reduce Apo-B levels, most studies also report a lack of significant further reduction of Apo-B levels with added omega-3 fatty acid treatment.

Hong et al. investigated the effects of fish oil and simvastatin in patients with coronary heart disease and mixed dyslipidemia. Patients having baseline triglyceride levels of 292.8 mg/dl or 269.5 mg/dl were initially treated with 10-20 mg/day simvastatin for 6-12 weeks. Thereafter the patients were treated with simvastatin and placebo or simvastatin and 3 g/day fish oil (Meilekang™). Combined treatment significantly reduced triglyceride levels, as compared to baseline and placebo. In addition, combined treatment numerically increased HDL-C levels, and numerically reduced LDL-C levels, as compared to baseline. However, the changes in HDL-C levels and LDL-C levels were not statistically significant. Levels of Apo-B were raised in the combined treatment group, while the Apo-B levels numerically decreased in the placebo group. Hong et al., *Chin. Med. Sci. J.* 19:145-49 (2004).

Contacos et al. investigated the effects of fish oil and pravastatin on patients with mixed hyperlipidemia. Patients having baseline triglyceride levels of 4.6 to 5.5 mmol/l (404 to 483 mg/dl) were initially treated for 6 weeks with 40 mg/day pravastatin, 6 g/day fish oil (Himega™, containing 3 g of omega-3 fatty acids, with an EPA/DHA ratio of 2:1), or placebo. Thereafter, all patients were treated with pravastatin and fish oil for an additional 12 weeks. Initial treatment with pravastatin significantly reduced LDL-C levels. Combined treatment of pravastatin and fish oil also significantly reduced triglyceride and LDL-C levels. However, the addition of fish oil to pravastatin monotherapy resulted in only a numerical increase in LDL-C levels, which was not statistically significant. Treatment with fish oil alone significantly reduced triglyceride levels, but increased LDL-C levels. Combined treatment for this group significantly reduced LDL-C levels, as compared to fish oil alone (but not as compared to baseline). Apo-B levels were significantly reduced with pravastatin treatment. Combination treatment with fish oil further numerically reduced Apo-B levels, however it was reported that this further reduction was not significant as compared to pravastatin monotherapy. Contacos et al., *Arterioscl. Thromb.* 13:1755-62 (1993).

Grekas et al. reported on the combined treatment of low-dose pravastatin and fish oil in post-renal transplantation dislipidemia. Thirty renal transplant patients with persistent hypercholesterolemia (total cholesterol >200 mg/dl) and on immunosuppressive therapy were given a standard diet for 4 weeks, followed by 8 weeks of therapy with 20 mg pravastatin. Baseline triglyceride levels at the diet stage were 184 mg/dl. This period was followed by an additional 4 weeks of standard diet, then 8 weeks of therapy with 20 mg pravastatin plus 1 g fish oil (Prolipid). Baseline triglyceride levels at the diet stage were 169 mg/dl. Apo-B levels were not significantly reduced with diet+statin therapy. However, diet+statin+fish oil was reported to significantly reduce Apo-B levels. Grekas et al., *Nephron* (2001) 88: 329-333. The Grekas et al. study results seem dubious, given that the study did not show a significant reduction in Apo-B levels with pravastatin therapy alone. PRAVACHOL® (pravastatin) is indicated as an adjunct to diet to reduce elevated Apo-B levels in patients with primary hypercholesterolemia and mixed dyslipidemia. Thus, the fact that the Grekas et al. study did not see significant Apo-B reduction with pravastatin makes the study results subject to doubt.

Huff et al. found that the combination of dietary fish oil and lovastatin reduces Apo-B levels in both very low-density lipoprotein (VLDL) and low density lipoprotein (LDL) fractions in miniature pigs. However, the study only compared combination treatment versus fish oil monotherapy, and did not compare combination treatment versus statin monotherapy. Huff et al., *Arteroscl. Thromb.*, 12(8): 901-910 (August 1992).

Jula et al. studied the effects of diet and simvastatin on various serum lipids in hypercholesterolemic men. After an open placebo period, subjects were allocated to a "habitual diet" or "dietary treatment" group. The dietary treatment consisted of a Mediterranean-type diet in which no more than 10% energy was from saturated and trans-unsaturated fatty acids; cholesterol intake was no more than 250 mg/day; omega-3 fatty acid intake of plant and marine origin was at least 4 g/day, and the ratio of omega-6 fatty acids to omega-3 fatty acids was less than 4; and intake of fruits, vegetables and soluble fiber was increased. Subjects were then also allocated to receive 20 mg/day simvastatin or placebo for 12 weeks in a double-blind, crossover fashion. Subjects in the dietary treatment group and the simvastatin group had significant reductions in Apo-B levels. The interaction between the two variables was reported as significant. Jula et al., *JAMA* 287 (5): 598-605 (2002).

U.S. Patent Application Publication No. 2003/0170643 claims a method of treating a patient, by administering a therapeutic which lowers plasma concentrations of Apo-B and/or an Apo-B-containing lipoprotein and/or a component of an atherogenic lipoprotein by stimulating post-ER presecretory proteolysis (PERPP).

Studies have investigated the effect of statins and Omacor® omega-3 fatty acids. For example, Hansen et al. investigated the effect of lovastatin (40 mg/day) in combination with 6 g/day Omacor® omega-3 fatty acids in patients with hypercholesterolemia. Patients having baseline triglyceride levels of 1.66 mmol/l (about 146 mg/dl) were treated with 6 g/day Omacor® for 6 weeks, followed by 40 mg/day lovastatin for an additional 6 weeks, and a combination of both Omacor® and lovastatin for a final 6 weeks. Lovastatin monotherapy resulted in significant increases in HDL-C levels, and significant decreases in triglyceride and LDL-C levels. After combination treatment, triglyceride and LDL-C levels were further significantly decreased. Apo-B levels were significantly reduced with lovastatin monotherapy, and further numerically reduced with the addition of omega-3 fatty acids, although such further reduction was not indicated as being significant as compared to lovastatin monotherapy. Hansen et al., *Arterioscl. Thromb.* 14(2): 223-229 (February 1994).

Nordoy et al. investigated the effect of atorvastatin and omega-3 fatty acids on patients with hyperlipemia. Patients having baseline triglyceride levels of 3.84 mmol/l (about 337 mg/dl) or 4.22 mmol/l (about 371 mg/dl) were treated with 10 mg/day atorvastatin for 5 weeks. Thereafter, for an additional 5 weeks, atorvastatin treatment was supplemented with 2 g/day Omacor® or placebo. Atorvastatin monotherapy, significantly increased HDL-C levels, and triglyceride, LDL-C and Apo-B levels significantly decreased, as compared to baseline. Combination treatment further increased HDL-C levels, as compared to atorvastatin alone. Triglyceride, LDL-C and Apo-B levels numerically further declined slightly with combination treatment, as compared to atorvastatin monotherapy; however, the decrease was not significant. Nordoy et al., *Nutr. Metab. Cardiovasc. Dis.* (2001) 11:7-16.

Chan et al. studied the combined treatment of atorvastatin (40 mg/day) and 4 g/day 4 Omacor® on obese, insulin-resistant men with dyslipidemia studied in a fasted state. Patients having baseline triglyceride levels of 1.7 to 2.0 mmol/l (about 150 to 170 mg/dl) were treated for 6 weeks with: 40 mg/day atorvastatin and placebo; 4 g/day Omacor® and placebo; a combination of atorvastatin and Omacor®; or a combination of placebos. Atorvastatin monotherapy significantly decreased Apo-B levels. Combination treatment also significantly decreased Apo-B levels, as compared to the placebo group. However, the effects attributable to the Omacor® were not significant. Chan et al., *Diabetes,* 51: 2377-2386 (August 2002).

Nordoy et al. investigated the effectiveness of combination treatment of 40 mg/day lovastatin and 6 g/day Omacor® (identified as "K-85") in patients with familial hypercholesterolemia, but who were without cardiovascular disease. The study included three intervention periods, each 6 weeks long, interrupted by washout periods of 6 weeks. The final test was carried out 12 weeks after the last intervention. Apo-B levels numerically reduced slightly with omega-3 fatty acid monotherapy, and were significantly reduced with lovastatin monotherapy. The combination treatment also significantly reduced Apo-B levels, as compared to baseline. However, the reduction was not indicated as being significant as compared to lovastatin monotherapy. Nordoy et al., *Essent. Fatty Acids Eicosanoids,* Invited Pap. Int'l Congr. $4^{th}$, 256-61 (1998).

Nordoy et al. also investigated the efficiency and the safety of treatment with simvastatin and omega-3 fatty acids in patients with hyperlipidemia. Patients having baseline triglyceride levels of 2.76 mmol/l (about 243 mg/dl) or 3.03 mmol/l (about 266 mg/dl) were treated for 5 weeks with 20 mg/day simvastatin or placebo, then all patients were treated for an additional 5 weeks with 20 mg/day simvastatin. Thereafter, patients were additionally treated with 4 g/day Omacor® or placebo, for a further 5 weeks. The administration of omega-3 fatty acids with simvastatin resulted in moderate reductions in serum total cholesterol and reduction in triglycerol levels, and a small numerical decrease in Apo-B levels. However, the effect attributable to the omega-3 fatty acids was not significant. Nordoy et al., *J. of Internal Medicine,* 243:163-170 (1998).

Durrington et al. examined the effectiveness, safety, and tolerability of a combination of Omacor® omega-3 acids and simvastatin in patients with established coronary heart disease and persisting hypertriglyceridemia. Patients having an average baseline triglyceride level >2.3 mmol/l (average patient serum triglyceride level was 4.6 mmol/l in the Omacor® group), were treated with 10-40 mg/day simvastatin (average dose in the Omacor® group was 33.3 mg/day) and 4 g/day Omacor® (2 g twice a day) or placebo, for 24 weeks in a double-blind trial, after which both groups were invited to receive Omacor® for a further 24 weeks in an open study. Combination treatment significantly decreased triglyceride levels within 12 weeks, as compared to baseline monotherapy. In addition, the VLDL cholesterol levels in these patients decreased by 30-40%. LDL-C levels significantly decreased, as compared to baseline monotherapy, only after 48 weeks, although there was a numerical (statistically insignificant) decrease at 12 and 24 weeks. Apo-B levels showed a slight numerical (statistically insignificant) decrease with addition of omega-3 fatty acids to simvastatin monotherapy. Durrington et al., *Heart,* 85:544-548 (2001).

SUMMARY OF THE INVENTION

There is an unmet need in the art for methods for the increased reduction of Apo-B levels over monotherapy with an HMG-CoA inhibitor alone. This method is especially useful in the treatment of one or more of the following: hypertriglyceridemia, hypercholesterolemia, mixed dyslipidemia, vascular disease, atherosclerotic disease and related conditions, and/or for the prevention or reduction of cardiovascular and/or vascular events, in subjects such as human subjects.

Some embodiments of the present invention provide for a method of utilizing a combination of an HMG-CoA inhibitor and omega-3 fatty acids for the reduction of Apo-B levels, which is suitable for the treatment of one or more of the following: hypertriglyceridemia, hypercholesterolemia, mixed dyslipidemia, vascular disease, atherosclerotic disease and related conditions, and/or for the prevention or reduction of cardiovascular and/or vascular events.

Some embodiments according to the present invention include a method of lipid therapy in a subject comprising administering to the subject an effective amount of an HMG-CoA inhibitor and omega-3 fatty acids, wherein an Apo-B level in the subject is reduced as compared to treatment with the HMG-CoA inhibitor alone.

In other embodiments, the present invention includes a method of reducing an Apo-B level in a subject group, comprising providing a subject group, and reducing the Apo-B level of the subject group by administering to the subject group a combination of an HMG-CoA inhibitor and omega-3 fatty acids in an amount effective to reduce the Apo-B level of the subject group as compared to treatment with an HMG-CoA inhibitor alone. In preferred embodiments, the subject group has at least one of the following conditions: hypertriglyceridemia, hypercholesterolemia, mixed dyslipidemia, vascular disease, and/or atherosclerotic disease and related conditions.

In further embodiments, the HMG-CoA inhibitor and the omega-3 fatty acids are administered as a single pharmaceutical composition as a combination product, for example, a unit dosage, comprising the HMG-CoA inhibitor and the omega-3 fatty acids.

In variations of the present invention, the HMG-CoA inhibitor is selected from the group consisting of pitavastatin, atorvastatin, rosuvastatin, fluvastatin, lovastatin, pravastatin and simvastatin.

In preferred embodiments the pharmaceutical composition(s) comprise Lovaza™ omega-3 fatty acids, as described in U.S. Pat. Nos. 5,502,077, 5,656,667 and 5,698,594. In other preferred embodiments the pharmaceutical composition(s) comprise omega-3 fatty acids present in a concentration of at least 40% by weight as compared to the total fatty acid content of the composition(s).

In still other preferred embodiments the omega-3 fatty acids comprise at least 50% by weight of EPA and DHA as compared to the total fatty acid content of the composition, and the EPA and DHA are in a weight ratio of EPA:DHA of from 99:1 to 1:99, preferably from 1:2 to 2:1.

In preferred embodiments, the HMG-CoA inhibitor used in combination with omega-3 fatty acids is simvastatin.

In one aspect of the invention, the combination product is used in the treatment of subjects with primary hypertriglyceridemia or hypercholesterolemia or mixed dyslipidemia.

In yet further preferred embodiments of the present invention the triglyceride levels in the serum of the subject (or the subject group) prior to the first administration of the combination therapy of the HMG-CoA inhibitor and the omega-3 fatty acids, i.e., at baseline, is about 200 to about 499 mg/dl.

The invention also includes the use of an effective amount of an HMG-CoA inhibitor and omega-3 fatty acids for the manufacture of a medicament useful for any of the treatment methods indicated herein.

Other features and advantages of the present invention will become apparent to those skilled in the art upon examination of the following or upon learning by practice of the invention.

DESCRIPTION OF THE PREFERRED EMBODIMENTS

The present invention is preferably directed to the utilization of HMG-CoA inhibitors and omega-3 fatty acids for reduction of Apo-B levels beyond that which is obtained with treatment of the HMG-CoA inhibitor alone. The methods of the present invention are especially useful for the treatment of one or more of the following: hypertriglyceridemia, hypercholesterolemia, mixed dyslipidemia, vascular disease, atherosclerotic disease and related conditions, and/or for the prevention or reduction of cardiovascular and/or vascular events.

In preferred embodiments of the invention, a subject has baseline Apo-B levels of greater than 0.9 g/l, and the use of the invention reduces the Apo-B levels to less than 0.9 g/l.

In some embodiments, a subject has non-HDL-C levels of at least 130 mg/dl, more preferably at least 160 mg/dl, and the use of the invention reduces the Apo-B levels, preferably by at least 2% as compared to baseline and/or further than treatment with the HMG-CoA inhibitor alone.

In some embodiments, a subject has elevated LDL-C levels (e.g., at least 100 mg/dl, at least 100 mg/dl and less than 130 mg/dl, at least 130 mg/dl, or at least 160 mg/dl) and/or elevated triglyceride levels (e.g., at least 150 mg/dl, at least 200 mg/dl, 200-499 mg/dl, or at least 500 mg/dl) and, if both, can be qualified as a subject with mixed dyslipidemia.

In some embodiments, the invention provides a novel combination. In a preferred embodiment, the combination comprises omega-3 fatty acids and an HMG-CoA inhibitor, wherein the omega-3 fatty acids are administered simultaneous to administration of the HMG-CoA inhibitor, e.g., as a single fixed dosage pharmaceutical composition or as separate compositions administered at the same time.

In other preferred embodiments, the administration comprises omega-3 fatty acids and an HMG-CoA inhibitor, wherein the omega-3 fatty acids are administered apart from the administration of the HMG-CoA inhibitor, but in a concomitant treatment regime. For example, the HMG-CoA inhibitor may be administered once daily while the omega-3 fatty acids are administered twice daily. One skilled in the art with the benefit of the present disclosure will understand that the precise dosage and schedule for the administration of the omega-3 fatty acids and the HMG-CoA inhibitor will vary depending on numerous factors, such as, for example, the route of administration, the seriousness of the condition, other comorbidities, and the use of other medications.

In some embodiments, the claimed method of administration is a first-line therapy, meaning that it is the first type of therapy given for the condition or disease. In other embodiments, the claimed method of administration is a second-line therapy, meaning that the treatment is given when initial treatment (first-line therapy, e.g., HMG-CoA inhibitor or omega-3 fatty acid treatment alone) does not work adequately with respect to treatment goals, or ceases to be adequate, e.g. due to physiological changes in the patient or changes in CHD risk factors.

In some embodiments, the invention is suitable for primary prevention. In other embodiments, the invention is suitable for secondary prevention.

In preferred embodiments, the selected subject group was receiving HMG-CoA inhibitor therapy prior to the combination therapy of the HMG-CoA inhibitor and the omega-3 fatty acids. Other active agents (other than omega-3 fatty acids) may also have been employed prior to the combination therapy of the HMG-CoA inhibitor and the omega-3 fatty acids.

In preferred embodiments, the present invention includes a method of lipid therapy in a subject group comprising administering to the subject group an effective amount of an HMG-CoA inhibitor and omega-3 fatty acids, wherein after administration to the subject group the triglyceride level and an Apo-B level of the subject group are reduced as compared to a control group treated with the HMG-CoA inhibitor alone, and preferably an HDL-C level of the subject group is increased as compared to a control group treated with the HMG-CoA inhibitor alone and/or as compared to baseline. Preferably, the subject group has a baseline triglyceride level of 200 to 499 mg/dl.

In other preferred embodiments, the present invention includes a method of lipid therapy in a subject group comprising administering to the subject group an effective amount of an HMG-CoA inhibitor and omega-3 fatty acids, wherein after administration to the subject group the triglyceride level and an Apo-B level of the subject group are reduced as compared to a control group treated with the HMG-CoA inhibitor alone, preferably without increasing LDL-C more than 1% as compared to baseline. Preferably, the subject group has a baseline triglyceride level of 200 to 499 mg/dl.

In other preferred embodiments, the present invention includes a method of lipid therapy in a subject group, comprising administering to the subject group an effective amount of an HMG-CoA inhibitor and omega-3 fatty acids, wherein after administration to the subject group at least one of the following: (a) a non-HDL-C level, (b) a total cholesterol level, (c) a triglyceride level, and (d) an Apo-B level of the subject group is reduced as compared to a control group treated with the HMG-CoA inhibitor alone, and preferably an HDL-C level of the subject group is increased as compared to a control group treated with the HMG-CoA inhibitor alone, preferably without increasing LDL-C more than 1% as compared to baseline.

In other preferred embodiments, the present invention includes a method of lipid therapy in a subject group comprising administering to the subject group an effective amount of an HMG-CoA inhibitor and omega-3 fatty acids, wherein after administration to the subject group a non-HDL-C level of the subject group is reduced as compared to a control group treated with the HMG-CoA inhibitor alone. Preferably, the subject group has a baseline triglyceride level of 200 to 499 mg/dl.

In other preferred embodiments, the invention includes a method of reducing a triglyceride level and an Apo-B level in a subject group without increasing an LDL-C level in the subject group, comprising providing a subject group, and reducing the triglyceride level and the Apo-B level of the subject group by administering to the subject group a combination of an HMG-CoA inhibitor and omega-3 fatty acids in an amount effective to reduce the triglyceride level and the Apo-B level of the subject group as compared to treatment with an HMG-CoA inhibitor alone without increasing the LDL-C level.

The phrase "compared to treatment with HMG-CoA inhibitor alone" can refer to treatment of the same subject or subject group, or treatment of a comparable subject or subject group (i.e., subject(s) within the same class with respect to a particular blood protein, lipid, or marker, such as a cholesterol or triglyceride level) in a different treatment group. The terms "reduce" and "increase" in accordance with the embodimented methods are intended to mean a statistically significant reduction or increase in accordance with its general and customary meaning, i.e., a probability of chance of 5% or less (p=0.05 or less), more preferably 2.5% or less (p=0.025 or less). In embodiments of the invention, the HMG-CoA inhibitor alone statistically significantly reduces or increases certain levels (such as reducing Apo-B levels), and the combination therapy of the HMG-CoA inhibitor and the omega-3 fatty acids further statistically significantly reduces or increases the levels.

In addition to reducing Apo-B levels, the methods and compositions of the invention may also be used to reduce one or more of the following blood protein, lipid, or marker levels in a treated subject or subject group, as compared to treatment with the HMG-CoA inhibitor alone: non-HDL-C levels, triglyceride levels, VLDL-C levels, total C levels, RLP-C levels, Lp-PLA2 levels and/or Apo-C3 levels. The methods and compositions of the invention may also be used to increase HDL-C levels, as compared to treatment with the HMG-CoA inhibitor alone. Preferably, the methods and compositions of the invention are utilized without increasing LDL-C levels, as compared to baseline.

Preferably, non-HDL-C levels may be reduced at least about 5%, preferably at least about 7%, from baseline and/or at least about 5%, preferably at least about 7%, further than treatment with the HMG-CoA inhibitor alone.

Preferably, the triglyceride levels may be reduced by at least about 20%, preferably at least about 25%, as compared to baseline and/or at least about 10%, preferably at least about 15%, more preferably at least about 20%, further than treatment with the HMG-CoA inhibitor alone.

Preferably, the VLDL-C levels may be reduced by at least about 15%, preferably at least about 20%, more preferably at least about 25%, as compared to baseline and/or at least about 10%, preferably at least about 15%, more preferably at least about 20%, further than treatment with the HMG-CoA inhibitor alone.

Preferably, the total C levels may be reduced by at least about 3%, preferably at least about 5%, as compared to baseline and/or at least about 2%, preferably at least about 3%, further than treatment with the HMG-CoA inhibitor alone.

Preferably, the RLP-C levels may be reduced by at least about 15%, preferably at least about 20%, as compared to baseline and/or at least about 10%, preferably at least about 15%, further than treatment with the HMG-CoA inhibitor alone.

Preferably, the Lp-PLA2 levels may be reduced by at least about 5%, preferably at least about 7%, more preferably at least about 10%, as compared to baseline and/or at least about 3%, preferably at least about 5%, more preferably at least about 7%, further than treatment with the HMG-CoA inhibitor alone.

Preferably, the Apo-B levels may be reduced by at least about 3%, preferably at least about 4%, as compared to baseline and/or at least about 1%, preferably at least about 2%, further than treatment with the HMG-CoA inhibitor alone.

Preferably, the Apo-C3 levels may be reduced by at least about 5%, preferably at least about 7%, as compared to baseline and/or at least about 8%, preferably at least about 10%, further than treatment with the HMG-CoA inhibitor alone.

Preferably, the HDL-C levels may be increased by at least about 2%, preferably at least about 3%, as compared to baseline and/or to treatment with the HMG-CoA inhibitor alone.

Preferably, the present invention also decreases the ratio of total cholesterol to HDL-C, preferably by at least about 5%, more preferably at least about 10%, as compared to baseline and/or at least about 5%, preferably at least about 10%, further than treatment with the HMG-CoA inhibitor alone.

Generally, the effect of the HMG-CoA inhibitor is dose dependent, i.e., the higher the dose, the greater the therapeutic affect. However, the effect of each HMG-CoA inhibitor is different, and therefore the level of therapeutic effect of one HMG-CoA inhibitor cannot be necessarily be directly correlated to the level of therapeutic effects of other HMG-CoA inhibitors. However, those of ordinary skill in the art would understand the correct dosage to be given to a particular subject, based on experience and the seriousness of the condition.

As used herein, the term "omega-3 fatty acids" includes natural or synthetic omega-3 fatty acids, or pharmaceutically acceptable esters, derivatives, conjugates (see, e.g., Zaloga et al., U.S. Patent Application Publication No. 2004/0254357, and Horrobin et al., U.S. Pat. No. 6,245,811, each hereby incorporated by reference), precursors or salts thereof and mixtures thereof. Examples of omega-3 fatty acid oils include but are not limited to omega-3 polyunsaturated, long-chain fatty acids such as a eicosapentaenoic acid (EPA), docosahexaenoic acid (DHA), and α-linolenic acid; esters of omega-3 fatty acids with glycerol such as mono-, di- and triglycerides; and esters of the omega-3 fatty acids and a primary, secondary or tertiary alcohol such as fatty acid methyl esters and fatty acid ethyl esters. Preferred omega-3 fatty acid oils are long-chain fatty acids such as EPA or DHA, triglycerides thereof, ethyl esters thereof and mixtures thereof. The omega-3 fatty acids or their esters, derivatives, conjugates, precursors, salts and mixtures thereof can be used either in their pure form or as a component of an oil such as fish oil, preferably purified fish oil concentrates. Commercial examples of omega-3 fatty acids suitable for use in the invention include Incromega F2250, F2628, E2251, F2573, TG2162, TG2779, TG2928, TG3525 and E5015 (Croda International PLC, Yorkshire, England), and EPAX6000FA, EPAX5000TG, EPAX4510TG, EPAX2050TG, K85TG, K85EE, K80EE and EPAX7010EE (Pronova Biocare a.s., 1327 Lysaker, Norway).

Preferred compositions include omega-3 fatty acids as recited in U.S. Pat. Nos. 5,502,077, 5,656,667 and 5,698,694, which are hereby incorporated herein by reference in their entireties.

Another preferred composition includes omega-3 fatty acids present in a concentration of at least 40% by weight, preferably at least 50% by weight, more preferably at least 60% by weight, still more preferably at least 70% by weight, most preferably at least 80% by weight, or even at least 90% by weight. Preferably, the omega-3 fatty acids comprise at least 50% by weight of EPA and DHA, more preferably at least 60% by weight, still more preferably at least 70% by weight, most preferably at least 80%, such as about 84% by weight. Preferably the omega-3 fatty acids comprise about 5 to about 100% by weight, more preferably about 25 to about 75% by weight, still more preferably about 40 to about 55% by weight, and most preferably about 46% by weight of EPA. Preferably the omega-3 fatty acids comprise about 5 to about 100% by weight, more preferably about 25 to about 75% by weight, still more preferably about 30 to about 60% by weight, and most preferably about 38% by weight of DHA. All percentages above are by weight as compared to the total fatty acid content in the composition, unless otherwise indicated. The percentage by weight may be based on the free acid or ester forms, although it is preferably based on the ethyl ester form of the omega-3 fatty acids even if other forms are utilized in accordance with the present invention.

The EPA:DHA ratio may be from 99:1 to 1:99, preferably 4:1 to 1:4, more preferably 3:1 to 1:3, most preferably 2:1 to 1:2. The omega-3 fatty acids may comprise pure EPA or pure DHA.

The omega-3 fatty acid composition optionally includes chemical antioxidants, such as alpha tocopherol, oils, such as soybean oil and partially hydrogenated vegetable oil, and lubricants such as fractionated coconut oil, lecithin and a mixture of the same.

The most preferred form of omega-3 fatty acids is the Lovaza™ omega-3 acid (K85EE, Pronova Biocare a.s., Lysaker, Norway) and preferably comprises the following characteristics (per dosage form):

| Test | Minimum Value | Maximum Value |
|---|---|---|
| Eicosapentaenoic acid C20:5 | 430 mg/g | 495 mg/g |
| Docosahexaenoic acid C22:6 | 347 mg/g | 403 mg/g |
| EPA and DHA | 800 mg/g | 880 mg/g |
| Total n-3 fatty acids | 90% (w/w) | |

The combination product of an HMG-CoA inhibitor and concentrated omega-3 fatty acids may be administered in a capsule, a tablet, a powder that can be dispersed in a beverage, or another solid oral dosage form, a liquid, a soft gel capsule, a coated soft gel capsule (see U.S. application Ser. No. 11/716,020, hereby incorporated by reference) or other convenient dosage form such as oral liquid in a capsule, as known in the art. In some embodiments, the capsule comprises a hard gelatin. The combination product may also be contained in a liquid suitable for injection or infusion.

The active ingredients of the present invention may also be administered with a combination of one or more non-active pharmaceutical ingredients (also known generally herein as "excipients"). Non-active ingredients, for example, serve to solubilize, suspend, thicken, dilute, emulsify, stabilize, preserve, protect, color, flavor, and fashion the active ingredients into an applicable and efficacious preparation that is safe, convenient, and otherwise acceptable for use.

Excipients include surfactants, such as propylene glycol monocaprylate, mixtures of glycerol and polyethylene glycol esters of long fatty acids, polyethoxylated castor oils, glycerol esters, oleoyl macrogol glycerides, propylene glycol monolaurate, propylene glycol dicaprylate/dicaprate, polyethylene-polypropylene glycol copolymer, and polyoxyethylene sorbitan monooleate, cosolvents such ethanol, glycerol, polyethylene glycol, and propylene glycol, and oils such as coconut, olive or safflower oils. The use of surfactants, cosolvents, oils or combinations thereof is generally known in the pharmaceutical arts, and as would be understood to one skilled in the art, any suitable surfactant may be used in conjunction with the present invention and embodiments thereof.

The omega-3 fatty acids can be administered in a daily amount of from about 0.1 g to about 10 g, more preferably about 1 g to about 8 g, and most preferably from about 2 g to about 6 g. In one embodiment, the omega-3 fatty acids are administered in an amount up to 4 g/day.

The HMG-CoA inhibitor may be administered in an amount more than, equal to or less than the conventional full-strength dose as a single-administered product. For example, the HMG-CoA inhibitor may be administered in an amount of from 10-100%, preferably about 25-100%, most preferably about 50-80%, of the conventional full-strength dose as a single-administered product. In one embodiment of the present invention, the HMG-CoA inhibitor can generally be present in an amount from about 0.5 mg to 80 mg, more preferably from about 1 mg to about 40 mg, and most preferably from about 2.5 mg to about 20 mg, per gram of omega-3 fatty acids. The daily dose may range from about 2 mg to about 320 mg, preferably about 4 mg to about 160 mg.

In some variations of the present invention, the combination of HMG-CoA inhibitor and the omega-3 fatty acids is formulated into a single administration or unit dosage.

Pravastatin, which is known in the market as Pravachol® manufactured by Bristol-Myers Squibb, Princeton, N.J., is hydrophilic. Pravastatin is best absorbed without food, i.e., an empty stomach. The dosage of pravastatin, in the combined administration of concentrated omega-3 fatty acids is preferably from 2.5 to 80 mg, preferably 5 to 60, and more preferably from 10 to 40 mg per dosage of concentrated omega-3 fatty acids. In one variation, the combination product using pravastatin is taken at or around bedtime, e.g., 10 μm.

Lovastatin, which is marketed under the name Mevacor® by Merck, Whitehouse Station, N.J., is hydrophobic. Unlike pravastatin, lovastatin should be taken with meals and accordingly, in some embodiments, the combination product of concentrated omega-3 fatty acids and lovastatin should be taken with food. The dosage of lovastatin, in the combined administration of concentrated omega-3 fatty acids is preferably from 2.5 to 100 mg, preferably 5 to 80 mg, and more preferably from 10 to 40 mg per dosage of concentrated omega-3 fatty acids.

Simvastatin, which is marketed under the name Zocor® by Merck, Whitehouse Station, N.J., is hydrophobic. The dosage of simvastatin, in the combined administration of concentrated omega-3 fatty acids is preferably from 1 to 80 mg per day, preferably 2 to 60 mg, and more preferably from 5 to 40 mg per dosage of concentrated omega-3 fatty acids.

Atorvastatin, which is marketed under the name Lipitor® by Pfizer, New York, N.Y., is hydrophobic and is known as a synthetic statin. The dosage of atorvastatin, in the combined administration of concentrated omega-3 fatty acids is preferably from 2.5 to 100 mg, preferably 5 to 80 mg, and more preferably from 10 to 40 mg per dosage of concentrated omega-3 fatty acids.

Fluvastatin, which is marketed under the name Lescol® by Novartis, New York, N.Y., is hydrophilic and is known as a synthetic statin. The dosage of fluvastatin, in the combined administration of concentrated omega-3 fatty acids is from 5 to 160 mg, preferably 10 to 120 mg, and more preferably from 20 to 80 mg per dosage of concentrated omega-3 fatty acids.

Rosuvastatin is marketed under the name Crestor® by Astra Zeneca, Wilmington, Del. The dosage of rosuvastatin, in the combined administration of concentrated omega-3 fatty acids is from 1 to 80 mg, preferably 2 to 60 mg, and more preferably from 5 to 40 mg per dosage of concentrated omega-3 fatty acids.

Pitavastatin is currently marketed in Japan. The dosage of pitavastatin, in the combined administration of omega-3 fatty acids is from 0.25 to 20 mg, preferably 0.5 to 10 mg, and more preferably from 1 to 7.5 mg per dosage of omega-3 fatty acids.

The daily dosages of HMG-CoA inhibitor and concentrated omega-3 fatty acids can be administered together in from 1 to 10 dosages, with the preferred number of dosages from 1 to 4 times a day, most preferred 1 to 2 times a day. The administration is preferably oral administration, although other forms of administration that provides a unit dosage of HMG-CoA inhibitor and concentrated omega-3 fatty acids may be used.

In some embodiments, the formulations of the present invention allow for improved effectiveness of each active ingredient, with one or both administered as a conventional full-strength dose, as compared to the formulations in the prior art. In other embodiments, the formulations of the present invention may allow for reduced dosages of HMG-CoA inhibitor and/or omega-3 fatty acids, as compared to the formulations in the prior art, while still maintaining or even improving upon the effectiveness of each active ingredient.

The present combination of an HMG-CoA inhibitor and omega-3 fatty acids may allow for a greater effect than any expected combined or additive effect of the two drugs alone. Moreover, the combined or additive effect of the two drugs may depend on the initial level of triglycerides in the blood of a subject. For example, the triglyceride level of a subject is generally as normal if less than 150 mg/dL, borderline to high if within about 150-199 mg/dL, high if within about 200-499 mg/dL and very high if 500 mg/dL or higher. The present invention may be used to reduce the triglyceride level of a "very high" down to a "high" or "borderline to high" in less than 48 weeks, preferably within 24 weeks, more preferably within 12 weeks, and most preferably within 8 weeks. The present invention may also be used to reduce the triglyceride level of a "high" down to a "borderline to high" or "normal" in less than 48 weeks, preferably within 24 weeks, more preferably within 12 weeks, and most preferably within 8 weeks.

EXAMPLES

Clinical Study: a Randomized, Double-Blind, Placebo-Controlled Study to Assess the Efficacy and Safety of Combined Lovaza™ and Simvastatin Therapy in Hypertriglyceridemic Subjects A randomized, double-blind, placebo-controlled clinical study was conducted to assess the efficacy and safety of combined treatment with Lovaza™ omega-3 fatty acids and simvastatin (Zocor®) in hypertriglyceridemic subjects. Patients were initially treated with 40 mg/day simvastatin for at least 8 weeks, whereupon baseline measurements were taken. Patients were eligible for enrollment and randomization if their baseline triglyceride levels were above normal (≥150 mg/dl) and their LDL-C at most 10% above the NCEP ATP III goal. A total of 259 patients were randomized and received at least one dose of either Lovaza™ omega-3 fatty acids or placebo, and 229 of these patients had baseline triglyceride levels between 200 and 499 mg/dl. Initial treatment was thereafter followed by an additional 8 week treatment with either 4 g/day Lovaza™ omega-3 fatty acids or placebo, while continuing statin therapy, in a double-blind fashion. 243 patients completed the study.

The following Table 1 shows the results obtained for changes in various lipid and inflammatory parameters and markers.

TABLE 1

|  | Omacor treatment: median % change from baseline | Placebo treatment: median % change from baseline | Difference (% median) | p-value |
| --- | --- | --- | --- | --- |
| Non-HDL-C | −9.0% | −2.2% | −6.8% | <0.0001 |
| LDL-C | +0.7% | −2.8% | +3.5% | 0.0522 |
| Apo-B | −4.2% | −1.9% | −2.3% | 0.0232 |

TABLE 1-continued

|  | Omacor treatment: median % change from baseline | Placebo treatment: median % change from baseline | Difference (% median) | p-value |
|---|---|---|---|---|
| TG | −29.5% | −6.3% | −23.2% | <0.0001 |
| VLDL-C | −27.5% | −7.2% | −20.3% | <0.0001 |
| total C | −4.8% | −1.7% | −3.1% | 0.0013 |
| HDL-C | +3.4% | −1.2% | +4.6% | <0.0001 |
| TC/HDL | −9.6% | −0.7% | −8.9% | <0.0001 |
| RLP-C | −36.0% | −10.6% | −25.4% | <0.0001 |
| Lp-PLA2 | −12.8% | −4.7% | −8.1% | 0.0019 |
| Apo-C3 | −7.8% | +3.9% | −11.7% | 0.0002 |

The following Tables 2 and 3 show the LDL-C goal achievement experienced in the study by those on Lovaza™ treatment and placebo, respectively.

TABLE 2

|  |  | Baseline | End of Treatment | |
|---|---|---|---|---|
|  |  |  | At or below goal | Above goal |
| Omacor treatment | At or below goal | 113 (92.62%) | 110 (97.35%) | 3 (2.65%) |
|  | Above goal | 9 (7.38%) | 3 (33.33%) | 6 (66.67%) |
|  | Total | 122 (100%) | 113 (92.62%) | 9 (7.38%) |

TABLE 3

|  |  | Baseline | End of Treatment | |
|---|---|---|---|---|
|  |  |  | At or below goal | Above goal |
| Placebo treatment | At or below goal | 120 (90.91%) | 117 (97.50%) | 3 (2.50%) |
|  | Above goal | 12 (9.09%) | 2 (16.67%) | 10 (83.33%) |
|  | Total | 132 (100%) | 119 (90.15%) | 13 (9.85%) |

A more detailed analysis of Apo-B reduction as function of baseline LDL-C and Non-HDL-C levels demonstrates the significant and increasing ability of Lovaza™ treatment to decrease Apo-B levels at increasing LDL-C and Non-HDL-C baseline levels, whereas placebo treatment results in random and insignificant changes in Apo-B levels.

Tables 4A, 4B and 5 show the Apo-B reduction and other lipid parameter changes with Lovaza™ or placebo treatment for specific LDL-C and Non-HDL-C patient subgroups. At higher LDL-C ($\geq$100 mg/dL) and Non-HDL-C ($\geq$130 mg/dL) baseline levels, Lovaza™ reduces Apo-B while at lower baseline levels, Apo-B changes by Lovaza™ versus placebo are insignificant. Table 4B shows that the Apo-B reducing effect is even more profound at higher LDL-C baseline levels, and seems to be accompanied by a reduction in LDL-C levels.

TABLE 4A

|  |  | LOVAZA (n = 87) | | Placebo (n = 89) | | |
|---|---|---|---|---|---|---|
|  | Lipid Parameters[†] | Baseline | % change | Baseline | % change | P-value |
| Patients with LDL-C <100 mg/dL | Non-HDL-C (mg/dL) | 126.7 | −8.6 | 126.3 | −2.5 | 0.0002 |
|  | Total-C (mg/dL) | 173.7 | −4.7 | 172.3 | −1.7 | 0.0289 |
|  | Triglycerides (mg/dL) | 270.0 | −29.1 | 273.0 | −7.0 | <0.0001 |
|  | VLDL-C (mg/dL) | 51.7 | −27.5 | 52.3 | −7.8 | <0.0001 |
|  | LDL-C (mg/dL) | 82.0 | 2.4 | 81.0 | −1.8 | 0.0108 |
|  | HDL-C (mg/dL) | 45.0 | 3.3 | 40.7 | −0.9 | <0.0001 |
|  | Apo-B (mg/dL) | 80.3 | −3.2 | 80.3 | −2.8 | 0.4220 |

|  |  | LOVAZA (n = 35) | | Placebo (n = 43) | | |
|---|---|---|---|---|---|---|
|  | Lipid Parameters[†] | Baseline | % change | Baseline | % change | P-value |
| Patients with LDL-C $\geq$100 mg/dL | Non-HDL-C (mg/dL)* | 159.5 | −10.2 | 167.1 | −1.0 | 0.0005 |
|  | Total-C (mg/dL)* | 208.2 | −7.1 | 215.7 | −1.2 | 0.0066 |
|  | Triglycerides (mg/dL)* | 270.6 | −28.1 | 269.4 | −1.8 | <0.0001 |
|  | VLDL-C (mg/dL)* | 51.4 | −25.4 | 52.1 | −2.2 | <0.0001 |
|  | LDL-C (mg/dL)* | 114.0 | −3.6 | 118.8 | −2.3 | 0.6503 |
|  | HDL-C (mg/dL)* | 48.7 | 3.5 | 48.6 | −1.4 | 0.0218 |
|  | Apo-B (mg/dL)* | 98.9 | −6.5 | 100.0 | 0.7 | 0.0016 |

TABLE 4B

| | Lipid Parameters[†] | LOVAZA (n = 30) | | Placebo (n = 33) | | |
|---|---|---|---|---|---|---|
| | | Baseline | % change | Baseline | % change | P-value |
| Patients with LDL-C ≥100 and <130 mg/dL | Non-HDL-C (mg/dL)* | 153.9 | −8.3 | 159.3 | −1.2 | 0.0138 |
| | Total-C (mg/dL)* | 201.0 | −5.8 | 207.3 | −1.2 | 0.0566 |
| | Triglycerides (mg/dL)* | 259.0 | −24.8 | 272.8 | −2.0 | <0.0001 |
| | VLDL-C (mg/dL)* | 50.6 | −23.5 | 52.7 | −3.2 | <0.0001 |
| | LDL-C (mg/dL)* | 110.3 | −2.3 | 111.6 | −2.3 | 0.9961 |
| | HDL-C (mg/dL)* | 47.1 | 3.0 | 48.0 | −0.6 | 0.1391 |
| | Apo-B (mg/dL)* | 96.0 | −5.4 | 96.6 | 0.4 | 0.0214 |

| | Lipid Parameters[†] | LOVAZA (n = 5) | | Placebo (n = 10) | | |
|---|---|---|---|---|---|---|
| | | Baseline | % change | Baseline | % change | P-value |
| Patients with LDL-C ≥130 mg/dL | Non-HDL-C (mg/dL)* | 193.3 | −21.3 | 192.8 | −0.2 | 0.0017 |
| | Total-C (mg/dL)* | 251.4 | −14.8 | 243.4 | −1.0 | 0.0098 |
| | Triglycerides (mg/dL)* | 340.3 | −47.8 | 258.2 | −1.0 | 0.0010 |
| | VLDL-C (mg/dL)* | 56.4 | −36.7 | 50.3 | 1.0 | 0.0087 |
| | LDL-C (mg/dL)* | 136.3 | −11.1 | 142.7 | −2.3 | 0.2180 |
| | HDL-C (mg/dL)* | 58.1 | 6.8 | 50.5 | −3.9 | 0.0258 |
| | Apo-B (mg/dL)* | 116.5 | −13.2 | 111.3 | 2.0 | 0.0127 |

[†]Variables typically not normally distributed, therefore statistical analyses were based on median values unless otherwise indicated
*Statistical analyses based on mean values due to normal distribution of the variables within the Subgroup

TABLE 5

| | Lipid Parameters[†] | LOVAZA (n = 47) | | Placebo (n = 52) | | |
|---|---|---|---|---|---|---|
| | | Baseline | % change | Baseline | % change | P-value |
| Patients with Non-HDL-C <130 mg/dL | Non-HDL-C (mg/dL) | 112.0 | −7.7 | 116.0 | −1.2 | 0.0066 |
| | Total-C (mg/dL) | 158.7 | −3.4 | 158.3 | −0.4 | 0.2453 |
| | Triglycerides (mg/dL)* | 272.1 | −30.1 | 255.4 | −4.1 | <0.0001 |
| | VLDL-C (mg/dL) | 47.7 | −28.5 | 48.0 | −7.7 | <0.0001 |
| | LDL-C (mg/dL) | 72.3 | 3.6 | 76.0 | −1.1 | 0.0056 |
| | HDL-C (mg/dL)* | 47.3 | 6.4 | 43.6 | −0.8 | 0.0003 |
| | Apo-B (mg/dL) | 73.7 | −1.7 | 75.2 | −0.9 | 0.8675 |

| | Lipid Parameters[†] | Omacor (n = 75) | | Placebo (n = 80) | | |
|---|---|---|---|---|---|---|
| | | Baseline | % change | Baseline | % change | P-value |
| Patients with Non-HDL-C ≥130 mg/dL | Non-HDL-C (mg/dL)* | 150.5 | −10.0 | 159.7 | −2.1 | <0.0001 |
| | Total-C (mg/dL)* | 197.9 | −6.9 | 205.1 | −2.0 | 0.0004 |
| | Triglycerides (mg/dL) | 272.3 | −29.1 | 286.8 | −5.0 | <0.0001 |
| | VLDL-C (mg/dL)* | 53.6 | −24.5 | 55.1 | −3.7 | <0.0001 |
| | LDL-C (mg/dL)* | 100.6 | −0.7 | 104.3 | −1.9 | 0.5476 |
| | HDL-C (mg/dL) | 46.7 | 2.0 | 44.8 | −1.0 | 0.0153 |
| | Apo-B (mg/dL)* | 92.6 | −5.9 | 95.4 | −0.4 | 0.0005 |

[†]Variables typically not normally distributed, therefore statistical analyses were based on median values unless otherwise indicated
*Statistical analyses based on mean values due to normal distribution of the variables within the subgroup Table 6 shows the Apo-B reduction and other lipid parameter changes with Lovaza™ or placebo treatment for above 200 mg/dL triglyceride baseline levels versus below this level. At higher triglyceride baseline levels (≥200 mg/dL), Lovaza™ reduces Apo-B while at lower baseline triglyceride levels, Apo-B changes by Lovaza™ versus placebo are insignificant.

TABLE 6

|  | Lipid Parameters† | LOVAZA (n = 11) | | Placebo (n = 10) | | |
|---|---|---|---|---|---|---|
|  |  | Baseline | % change | Baseline | % change | P-value |
| Patients with TG <200 mg/dL | Non-HDL-C (mg/dL)* | 130.5 | −7.8 | 135.6 | −3.9 | 0.4757 |
|  | Total-C (mg/dL)* | 183.0 | −4.0 | 190.4 | −4.6 | 0.8834 |
|  | Triglycerides (mg/dL)* | 186.2 | −25.2 | 189.1 | 4.6 | 0.0183 |
|  | VLDL-C (mg/dL)* | 37.2 | −24.9 | 37.9 | −1.1 | 0.0268 |
|  | LDL-C (mg/dL)* | 99.1 | −3.3 | 102.8 | −7.4 | 0.4498 |
|  | HDL-C (mg/dL)* | 52.6 | 5.2 | 54.8 | −5.8 | 0.0135 |
|  | Apo-B (mg/dL)* | 82.6 | −2.4 | 84.5 | −2.8 | 0.9353 |
|  |  | LOVAZA (n = 111) | | Placebo (n = 122) | | |
|  | Lipid Parameters† | Baseline | % change | Baseline | % change | P-value |
| Patients with TG ≥200 mg/dL | Non-HDL-C (mg/dL) | 137.7 | −9.3 | 141.7 | −1.9 | <0.0001 |
|  | Total-C (mg/dL) | 184.3 | −5.3 | 183.5 | −1.1 | 0.0007 |
|  | Triglycerides (mg/dL) | 272.3 | −30.2 | 274.7 | −6.3 | <0.0001 |
|  | VLDL-C (mg/dL) | 53.0 | −27.8 | 53.7 | −7.2 | <0.0001 |
|  | LDL-C (mg/dL) | 89.3 | 1.6 | 87.5 | −1.8 | 0.0587 |
|  | HDL-C (mg/dL) | 45.0 | 2.9 | 42.3 | −0.9 | 0.0001 |
|  | Apo-B (mg/dL) | 85.7 | −4.7 | 87.0 | −1.4 | 0.0117 |

†Variables typically not normally distributed, therefore statistical analyses were based on median values unless otherwise indicated
*Statistical analyses based on mean values due to normal distribution of the variables within the subgroup Tables 7 and 8 show the Apo-B reduction and other lipid parameter changes with Lovaza™ or placebo treatment for specific LDL-C/Triglyceride and Non-HDL-C/Triglyceride patient subgroups. At combined higher LDL-C (≥100 mg/dL) and triglyceride (≥200 mg/dL) baseline levels and at combined Non-HDL-C (≥130 mg/dL) and triglyceride (≥200 mg/dL) baseline levels, Lovaza™ reduces Apo-B while at lower baseline levels, Apo-B changes by Lovaza™ versus placebo are insignificant.

TABLE 7

|  | Lipid Parameters† | LOVAZA (n = 93) | | Placebo (n = 93) | | |
|---|---|---|---|---|---|---|
|  |  | Baseline | % change | Baseline | % change | P-value |
| Patients with LDL-C <100 mg/dL and/or TG <200 mg/dL | Non-HDL-C (mg/dL) | 129.7 | −7.9 | 128.3 | −2.3 | 0.0001 |
|  | Total-C (mg/dL) | 178.0 | −4.7 | 174.0 | −1.7 | 0.0171 |
|  | Triglycerides (mg/dL) | 266.3 | −29.1 | 269.0 | −6.3 | <0.0001 |
|  | VLDL-C (mg/dL) | 50.3 | −27.5 | 52.0 | −7.7 | <0.0001 |
|  | LDL-C (mg/dL) | 83.7 | 1.6 | 82.3 | −2.6 | 0.0177 |
|  | HDL-C (mg/dL) | 45.3 | 3.3 | 42.7 | −0.9 | <0.0001 |
|  | Apo-B (mg/dL) | 80.3 | −2.7 | 80.3 | −2.5 | 0.4178 |
|  |  | LOVAZA (n = 29) | | Placebo (n = 39) | | |
|  | Lipid Parameters† | Baseline | % change | Baseline | % change | P-value |
| Patients with LDL- | Non-HDL-C (mg/dL)* | 162.2 | −10.7 | 167.0 | −1.3 | 0.0012 |

TABLE 7-continued

| | | | | | | |
|---|---|---|---|---|---|---|
| C ≥100 mg/dL and TG ≥200 mg/dL | Total-C (mg/dL)* | 210.9 | −7.4 | 215.3 | −1.5 | 0.0130 |
| | Triglycerides (mg/dL)* | 287.4 | −28.8 | 278.1 | −3.7 | <0.0001 |
| | VLDL-C (mg/dL)* | 54.2 | −25.6 | 53.7 | −4.2 | <0.0001 |
| | LDL-C (mg/dL)* | 114.1 | −3.1 | 117.4 | −2.4 | 0.8053 |
| | HDL-C (mg/dL)* | 48.6 | 3.9 | 48.3 | −1.4 | 0.0204 |
| | Apo-B (mg/dL)* | 100.8 | −7.5 | 100.1 | 0.4 | 0.0013 |

†Variables typically not normally distributed, therefore statistical analyses were based on median values unless otherwise indicated
*Statistical analyses based on mean values due to normal distribution of the variables within the subgroup

TABLE 8

| | | LOVAZA (n = 54) | | Placebo (n = 56) | | |
|---|---|---|---|---|---|---|
| | Lipid Parameters† | Baseline | % change | Baseline | % change | P-value |
| Patients with Non-HDL-C <130 mg/Dl or TG <200 mg/dl | Non-HDL-C (mg/dL) | 116.2 | −7.6 | 117.7 | −0.9 | 0.0020 |
| | Total-C (mg/dL) | 162.2 | −3.4 | 161.0 | −0.7 | 0.1170 |
| | Triglycerides (mg/dL)* | 261.0 | −29.2 | 250.4 | −2.6 | <0.0001 |
| | VLDL-C (mg/dL) | 45.3 | −28.2 | 46.5 | −7.2 | <0.0001 |
| | LDL-C (mg/dL) | 73.7 | 2.5 | 76.8 | −1.6 | 0.0213 |
| | HDL-C (mg/dL)* | 47.9 | 5.9 | 44.2 | −0.9 | 0.0003 |
| | Apo-B (mg/dL) | 75.2 | −1.7 | 75.8 | −0.9 | 0.9953 |

| | | LOVAZA (n = 68) | | Placebo (n = 76) | | |
|---|---|---|---|---|---|---|
| | Lipid Parameters† | Baseline | % change | Baseline | % change | P-value |
| Patients with Non-HDL-C ≥130 mg/dL and TG ≥200 mg/dL | Non-HDL-C (mg/dL)* | 151.2 | −10.0 | 159.3 | −2.3 | <0.0001 |
| | Total-C (mg/dL)* | 198.1 | −7.0 | 204.4 | −2.2 | 0.0020 |
| | Triglycerides (mg/dL) | 280.5 | −29.5 | 290.2 | −5.9 | <0.0001 |
| | VLDL-C (mg/dL)* | 55.4 | −24.6 | 56.1 | −4.9 | <0.0001 |
| | LDL-C (mg/dL)* | 99.6 | −0.1 | 102.8 | −2.0 | 0.3863 |
| | HDL-C (mg/dL) | 46.2 | 1.8 | 44.5 | −1.0 | 0.0348 |
| | Apo-B (mg/dL) | 90.7 | −6.8 | 93.7 | −2.4 | 0.0025 |

†Variables typically not normally distributed, therefore statistical analyses were based on median values unless otherwise indicated
*Statistical analyses based on mean values due to normal distribution of the variables within the subgroup All references cited herein are hereby incorporated by reference in their entirety.

What is claimed is:

1. A method of reducing Apo-B and non-HDL-cholesterol levels in a subject group, comprising administering simvastatin and an omega-3 fatty acid composition in combination therapy to a subject group, comprising:
providing a subject group comprising one or more subjects which have been initially treated with 40 mg/day simvastatin for at least 8 weeks and having a baseline LDL-cholesterol level of not more than 10% above their NCEP ATP III goal after said initial treatment, with a baseline LDL-cholesterol level of at least 100 mg/dL, a baseline non-HDL-cholesterol level of at least 130 mg/dL, and a baseline triglyceride level of 200 to 499 mg/dL after said initial treatment, and reducing the Apo-B and the non-HDL-cholesterol levels of the subject group by administering to the subject group 4 g/day of the omega-3 fatty acid composition and 40 mg/day simvastatin for at least 8 weeks,
wherein the omega-3 fatty acid composition comprises at least 90% by weight omega-3 fatty acids, about 40% to about 55% by weight of the fatty acid EPA, about 30% to about 60% by weight of the fatty acid DHA, and at least 80% by weight EPA and DHA as compared to the total fatty acid content of the composition, and has an EPA:DHA weight ratio of 2:1 to 1:2, and wherein the omega-3 fatty acids in the composition comprise omega-3 polyunsaturated, long-chain fatty acids, esters of omega-3 fatty acids with glycerol, esters of omega-3 fatty acids and a primary, secondary or tertiary alcohol, or a mixture thereof, and wherein the Apo-B and non-HDL-cholesterol levels of the subject group are reduced by a statistically significant amount as compared to treatment with simvastatin alone.

2. The method of claim 1, wherein the subject group has at least one of the following conditions or diseases prior to said combination therapy: hypertriglyceridemia, hypercholesterolemia, mixed dyslipidemia, vascular disease, and atherosclerotic disease.

3. The method of claim 1, wherein the omega-3 fatty acid composition and the simvastatin are administered together in a unit dose form.

4. The method of claim 1, wherein an increase of the LDL-C level is avoided in the combination therapy.

5. The method of claim 1 wherein the subject group has a baseline LDL-cholesterol level of at least 130 mg/dL.

6. A method of reducing the Apo B level of a subject group, comprising administering simvastatin and an omega-3 fatty acid composition in combination therapy to a subject group, comprising:
   measuring LDL-cholesterol, non-HDL-cholesterol, and triglyceride levels in subjects,
   providing a subject group comprising one or more subjects which have been initially treated with 40 mg/day simvastatin for at least 8 weeks and having a baseline LDL-cholesterol level of not more than 10% above their NCEP ATP III goal after said initial treatment, with a baseline LDL-cholesterol level of at least 100 mg/dL, a baseline non-HDL-cholesterol level of at least 130 mg/dL, and a baseline triglyceride level of 200 to 499 mg/dL after said initial treatment, and
   reducing the Apo-B level of the subject group by administering to the subject group 4 g/day of the omega-3 fatty acid composition and 40 mg/day simvastatin for at least 8 weeks,
   wherein the omega-3 fatty acid composition comprises at least 90% by weight omega-3 fatty acids, about 40% to about 55% by weight of the fatty acid EPA, about 30% to about 60% by weight of the fatty acid DHA, and at least 80% by weight EPA and DHA as compared to the total fatty acid content of the composition, and has an EPA:DHA weight ratio of 2:1 to 1:2, and wherein the omega-3 fatty acids in the composition comprise omega-3 polyunsaturated, long-chain fatty acids, esters of omega-3 fatty acids with glycerol, esters of omega-3 fatty acids and a primary, secondary or tertiary alcohol, or a mixture thereof,
   and wherein the Apo-B level of the subject group is reduced by a statistically significant amount as compared to treatment with simvastatin alone and an increase of the LDL-cholesterol level is avoided in the combination therapy.

7. The method of claim 6, wherein the subject group has at least one of the following conditions or diseases prior to said combination therapy: hypertriglyceridemia, hypercholesterolemia, mixed dyslipidemia, vascular disease, and atherosclerotic disease.

8. The method of claim 6, wherein the omega-3 fatty acids and the statin are administered together in a unit dose form.

9. The method of claim 6, wherein an increase of the LDL-C level is avoided in the combination therapy.

10. The method of claim 6, wherein the subject group has a baseline LDL-cholesterol level of at least 130 mg/dL.

11. A method of reducing the Apo B level of a subject group, comprising administering simvastatin and an omega-3 fatty acid composition in combination therapy to a subject group, comprising:
   providing a subject group comprising one or more subjects which have been initially treated with 40 mg/day simvastatin for at least 8 weeks and having a baseline LDL-cholesterol level of not more than 10% above their NCEP ATP III goal after said initial treatment, with a baseline LDL-cholesterol level of at least 100 mg/dL, a baseline non-HDL-cholesterol level of at least 130 mg/dL, and a baseline triglyceride level of at least 200 to 499 mg/dL after said initial treatment,
   reducing the Apo-B level of the subject group by administering to the subject group 4 g/day of the omega-3 fatty acid composition and 40 mg/day simvastatin for at least 8 weeks,
   wherein the omega-3 fatty acid composition comprises at least 90% by weight omega-3 fatty acids, about 40% to about 55% by weight of the fatty acid EPA, about 30% to about 60% by weight of the fatty acid DHA, and at least 80% by weight EPA and DHA as compared to the total fatty acid content of the composition, and has an EPA:DHA weight ratio of 2:1 to 1:2, and wherein the omega-3 fatty acids in the composition comprise omega-3 polyunsaturated, long-chain fatty acids, esters of omega-3 fatty acids with glycerol, esters of omega-3 fatty acids and a primary, secondary or tertiary alcohol, or a mixture thereof,
   and determining the reduction in the Apo-B level of the subject group, wherein the Apo-B level of the subject group is reduced by a statistically significant amount as compared to treatment with simvastatin alone.

12. The method of claim 11, wherein the subject group has at least one of the following conditions or diseases prior to said combination therapy: hypertriglyceridemia, hypercholesterolemia, mixed dyslipidemia, vascular disease, and atherosclerotic disease.

13. The method of claim 11, wherein the omega-3 fatty acids and the statin are administered together in a unit dose form.

14. The method of claim 11, wherein an increase of the LDL-C level is avoided in the combination therapy.

15. The method of claim 11, wherein the subject group has a baseline LDL-cholesterol level of at least 130 mg/dL.

16. A method of reducing Apo-B and non-HDL-cholesterol levels in a subject, comprising administering simvastatin and an omega-3 fatty acid composition in combination therapy to the subject, comprising:
   providing a subject which has been initially treated with 40 mg/day simvastatin for at least 8 weeks, and after said initial treatment having a baseline LDL-cholesterol level of at least 100 mg/dL and not more than 10% above their NCEP ATP III goal, a baseline non-HDL-cholesterol level of at least 130 mg/dL, and a baseline triglyceride level of 200 to 499 mg/dL, and
   reducing the Apo-B and the non-HDL-cholesterol levels of the subject by administering to the subject 4 g/day of the omega-3 fatty acid composition and 40 mg/day simvastatin for at least 8 weeks,
   wherein the omega-3 fatty acid composition comprises at least 90% by weight omega-3 fatty acids, about 40% to about 55% by weight of the fatty acid EPA, about 30% to about 60% by weight of the fatty acid DHA, and at least 80% by weight EPA and DHA as compared to the total fatty acid content of the composition, and has an EPA:DHA weight ratio of 2:1 to 1:2, and wherein the omega-3 fatty acids in the composition comprise omega-3 polyunsaturated, long-chain fatty acids, esters of omega-3 fatty acids with glycerol, esters of omega-3 fatty acids and a primary, secondary or tertiary alcohol, or a mixture thereof, and wherein the Apo-B and non-HDL-cholesterol levels of the subject are reduced by a statistically significant amount as compared to treatment with simvastatin alone.

17. The method of claim 16, wherein the subject has at least one of the following conditions or diseases prior to said combination therapy: hypertriglyceridemia, hypercholesterolemia, mixed dyslipidemia, vascular disease, and atherosclerotic disease.

18. The method of claim 16, wherein the omega-3 fatty acids and the statin are administered together in a unit dose form.

19. The method of claim 16, wherein an increase of the subject's LDL-C level is avoided in the combination therapy.

20. The method of claim 16, wherein the subject has a baseline LDL-cholesterol level of at least 130 mg/dL.

21. A method of reducing the Apo B level of a subject, comprising administering simvastatin and an omega-3 fatty acid composition in combination therapy to the subject, comprising:

measuring LDL-cholesterol, non-HDL-cholesterol, and triglyceride levels in the subject, providing a subject which has been initially treated with 40 mg/day simvastatin for at least 8 weeks, and after said initial treatment having a baseline LDL-cholesterol level of at least 100 mg/dL and not more than 10% above their NCEP ATP III goal, a baseline non-HDL-cholesterol level of at least 130 mg/dL, and a baseline triglyceride level of 200 to 499 mg/dL, and reducing the Apo-B level of the subject by administering to the subject 4 g/day of the omega-3 fatty acid composition and 40 mg/day simvastatin for at least 8 weeks, wherein the omega-3 fatty acid composition comprises at least 90% by weight omega-3 fatty acids, about 40% to about 55% by weight of the fatty acid EPA, about 30% to about 60% by weight of the fatty acid DHA, and at least 80% by weight EPA and DHA as compared to the total fatty acid content of the composition, and has an EPA:DHA weight ratio of 2:1 to 1:2, and wherein the omega-3 fatty acids in the composition comprise omega-3 polyunsaturated, long-chain fatty acids, esters of omega-3 fatty acids with glycerol, esters of omega-3 fatty acids and a primary, secondary or tertiary alcohol, or a mixture thereof, and wherein the Apo-B level of the subject is reduced by a statistically significant amount as compared to treatment with simvastatin alone.

22. The method of claim 21, wherein the subject has at least one of the following conditions or diseases prior to said combination therapy: hypertriglyceridemia, hypercholesterolemia, mixed dyslipidemia, vascular disease, and atherosclerotic disease.

23. The method of claim 21, wherein the omega-3 fatty acids and the statin are administered together in a unit dose form.

24. The method of claim 21, wherein an increase of the subject's LDL-C level is avoided in the combination therapy.

25. The method of claim 21, wherein the subject has a baseline LDL-cholesterol level of at least 130 mg/dL.

26. A method of reducing the Apo B level of a subject, comprising administering simvastatin and an omega-3 fatty acid composition in combination therapy to the subject, comprising:

providing a subject which has been initially treated with 40 mg/day simvastatin for at least 8 weeks, and after said initial treatment having a baseline LDL-cholesterol level of at least 100 mg/dL and not more than 10% above their NCEP ATP III goal, a baseline non-HDL-cholesterol level of at least 130 mg/dL, and a baseline triglyceride level of at least 200 to 499 mg/dL, reducing the Apo-B level of the subject by administering to the subject 4 g/day of the omega-3 fatty acid composition and 40 mg/day simvastatin for at least 8 weeks, wherein the omega-3 fatty acid composition comprises at least 90% by weight omega-3 fatty acids, about 40% to about 55% by weight of the fatty acid EPA, about 30% to about 60% by weight of the fatty acid DHA, and at least 80% by weight EPA and DHA as compared to the total fatty acid content of the composition, and has an EPA:DHA weight ratio of 2:1 to 1:2, and wherein the omega-3 fatty acids in the composition comprise omega-3 polyunsaturated, long-chain fatty acids, esters of omega-3 fatty acids with glycerol, esters of omega-3 fatty acids and a primary, secondary or tertiary alcohol, or a mixture thereof, and determining the reduction in the Apo-B level of the subject, wherein the Apo-B level of the subject is reduced by a statistically significant amount as compared to treatment with simvastatin alone.

27. The method of claim 26, wherein the subject has at least one of the following conditions or diseases prior to said combination therapy: hypertriglyceridemia, hypercholesterolemia, mixed dyslipidemia, vascular disease, and atherosclerotic disease.

28. The method of claim 26, wherein the omega-3 fatty acids and the statin are administered together in a unit dose form.

29. The method of claim 26, wherein an increase of the subject's LDL-C level is avoided in the combination therapy.

30. The method of claim 26, wherein the subject has a baseline LDL-cholesterol level of at least 130 mg/dL.

* * * * *